United States Patent
Berrehail

(10) Patent No.: US 7,169,121 B2
(45) Date of Patent: Jan. 30, 2007

(54) ELASTIC DYNAMIC IMMOBILIZER FOR FINGERS OR TOES

(75) Inventor: Mohamed Berrehail, Meylan (FR)

(73) Assignee: Laboratoire Sober, Crolles (FR)

(*) Notice: Subject to any disclaimer, the term of this patent is extended or adjusted under 35 U.S.C. 154(b) by 365 days.

(21) Appl. No.: 10/610,916

(22) Filed: Jul. 2, 2003

(65) Prior Publication Data
US 2004/0144389 A1 Jul. 29, 2004

(30) Foreign Application Priority Data
Jul. 2, 2002 (FR) .................................. 02 08255

(51) Int. Cl.
*A61F 5/00* (2006.01)
(52) U.S. Cl. .............................. 602/22; 602/20; 602/32; 602/36; 602/38; 602/30
(58) Field of Classification Search ............... 602/22, 602/21, 20, 5, 6, 7, 30, 63, 41, 32, 36, 38, 602/60, 61; 128/878–880, 893, 894, 882; 2/21, 163; D24/190; 482/44, 47
See application file for complete search history.

(56) References Cited

U.S. PATENT DOCUMENTS

| | | | | |
|---|---|---|---|---|
| 2,354,770 A | * | 8/1944 | Patterson | 602/30 |
| 3,229,304 A | * | 1/1966 | Brooks | 2/21 |
| 3,421,761 A | * | 1/1969 | Richard | 473/61 |
| 4,270,528 A | * | 6/1981 | Hanson | 602/22 |
| 4,615,046 A | | 10/1986 | Martin | |
| D293,379 S | * | 12/1987 | Link | D24/190 |
| 4,770,166 A | * | 9/1988 | Garris | 602/22 |
| 5,095,897 A | * | 3/1992 | Clark et al. | 602/22 |
| 5,267,945 A | | 12/1993 | Doctor et al. | |
| 6,049,022 A | * | 4/2000 | Tseng et al. | 602/41 |
| 6,575,925 B1 | * | 6/2003 | Noble | 602/20 |
| 6,932,782 B2 | * | 8/2005 | Ferraioli | 602/22 |
| 2004/0019308 A1 | * | 1/2004 | Chow | 602/61 |

FOREIGN PATENT DOCUMENTS

| | | |
|---|---|---|
| FR | 2 578 740 | 9/1986 |
| SU | 1378827 A1 | 3/1988 |
| WO | WO 95/04512 * | 2/1995 |

* cited by examiner

*Primary Examiner*—Henry Bennett
(74) *Attorney, Agent, or Firm*—Oliff & Berridge, PLC

(57) ABSTRACT

The present invention relates to a medical device for syndactyly of at least two fingers or toes, said device being in one piece and comprising at least two rings joined via at least one connection bar in such a way as to permit sliding of the syndactylized fingers or toes relative to one another.

16 Claims, 4 Drawing Sheets

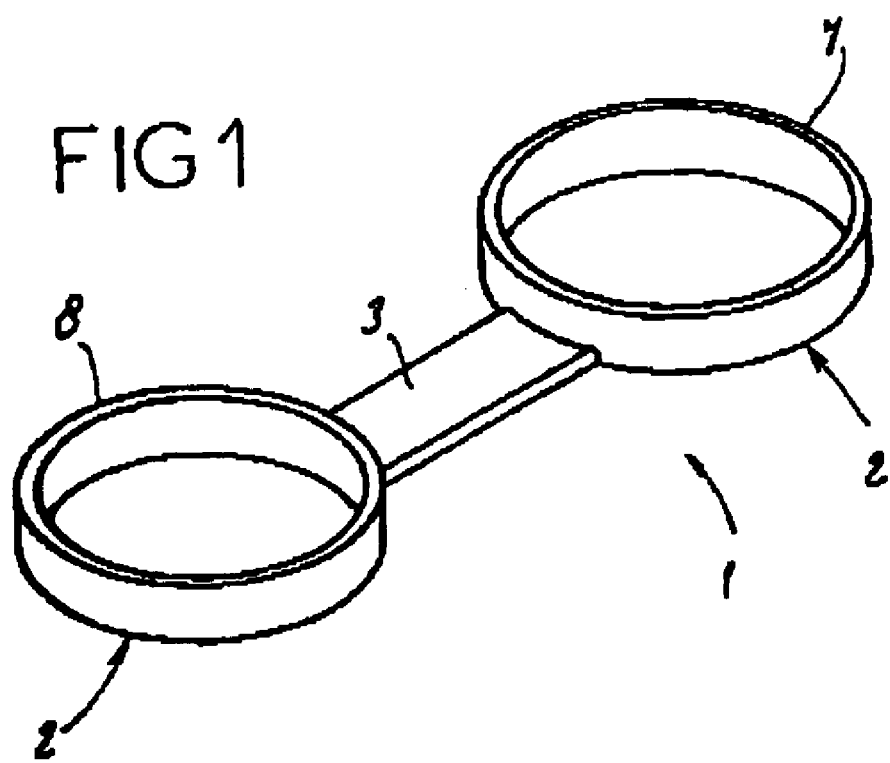

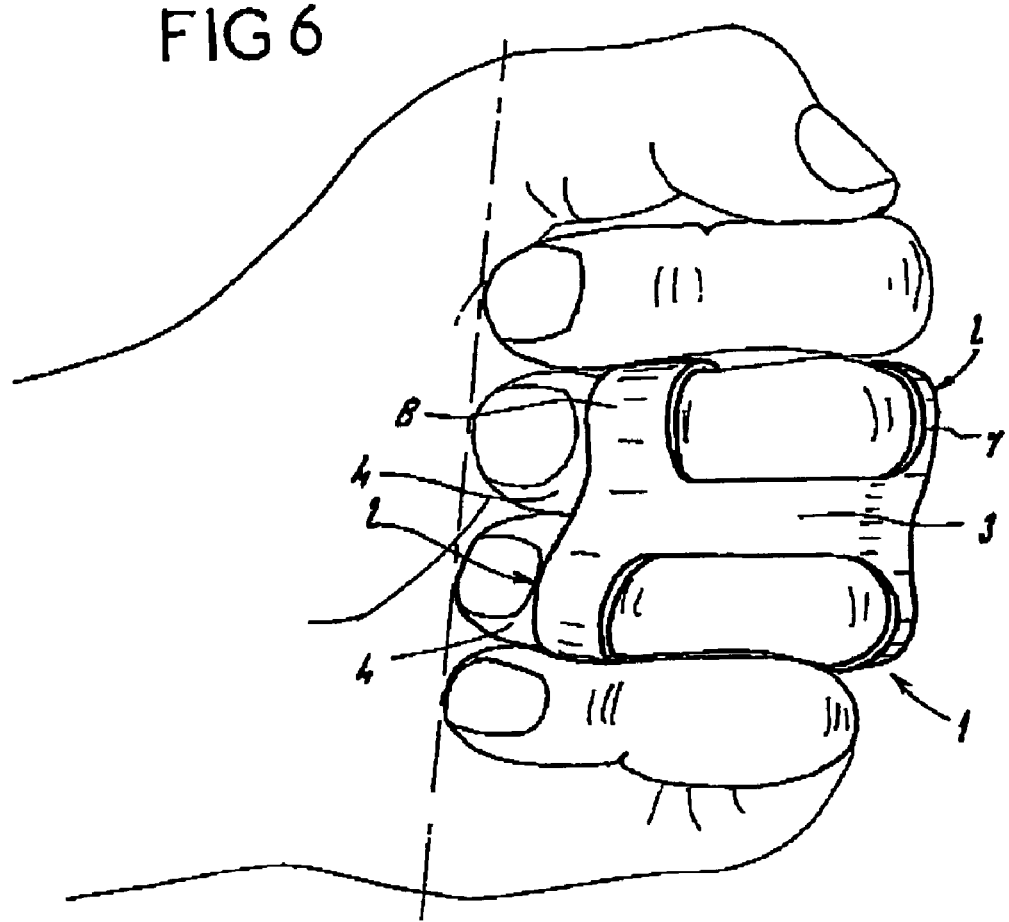

ELASTIC DYNAMIC IMMOBILIZER FOR FINGERS OR TOES

BACKGROUND OF THE INVENTION

The present invention relates to an elastic dynamic immobilizer for fingers or toes, permitting syndactyly of one or more fingers.

More particularly, the device according to the present invention is used for syndactyly of the last four fingers of the hand, or the toes.

DESCRIPTION OF THE PRIOR ART

By "syndactyly" we mean the medical procedure by which it is possible to temporarily and reversibly fix several fingers or toes of a hand, at least one injured finger to one healthy finger, so that the healthy finger serves as a support for the injured finger.

Syndactyly devices of this kind are used in therapy to repair injury of the fingers, metacarpals, toes or metatarsals (fractures, dislocations, sprains, wounds, burns, etc.). Syndactyly is also performed in rheumatology, in the case of certain inflammatory conditions. Syndactyly is in principle not performed on the thumb, given that the latter is an opposable finger, and, in view of its geometry in relation to the other fingers, it is quite difficult to perform syndactyly of the thumb with the index.

The medical devices used to perform syndactyly are usually made up of a splint of rigid plastic or metal covered with fabric, or semi-rigid devices made of adhesive fabric of the Elastoplast™ type or of self-sticking non-adhesive fabric of the Velcro® type.

A major disadvantage of such devices lies in the fact that they have no dynamic function for early rehabilitation during the healing period. In particular, they do not permit sliding of one finger relative to the other syndactylized fingers.

SUMMARY OF THE INVENTION

It is therefore an object of the present invention to make available a device permitting syndactyly of two or more fingers or toes, which device is economic to produce, easy to use, and permits early dynamic rehabilitation of the injured finger.

The abovementioned object is achieved with a medical device for syndactyly of at least two fingers or toes, said device being in one piece and comprising at least two flexible rings joined via at least one flexible connection bar in such a way as to permit sliding of the syndactylized fingers or toes relative to one another during flexion/extension movements.

According to one embodiment of the invention, the syndactyly device comprises two intersecting connection bars arranged between at least two rings. According to an alternative embodiment of the invention, it comprises at least two connection bars parallel to one another and arranged between at least two rings.

Each bar of the device is preferably a dorsal and/or lateral bar, and the rings of the device may also preferably be integral with a second device.

The device according to the invention is advantageously made of a single elastomeric material with resilient properties. This makes it possible to reduce the production costs and thus provide an effective device at less cost for the patient.

According to one embodiment of the invention, the syndactyly device is made of two materials, one flexible for the rings, and the other more rigid for the bar or bars.

DESCRIPTION OF THE DRAWINGS

In any case, the invention will be clearly understood from the following description in which reference is made to the attached diagrammatic drawing showing, by way of non-limiting examples, several preferred forms of the syndactyly device according to the invention.

FIG. 1 is a plan view, in perspective, of a first device with a single bar.

FIG. 6 is a perspective view of a device according to FIG. 1, when the fingers are flexed.

DESCRIPTION OF THE PREFERRED EMBODIMENTS

Figure 3:
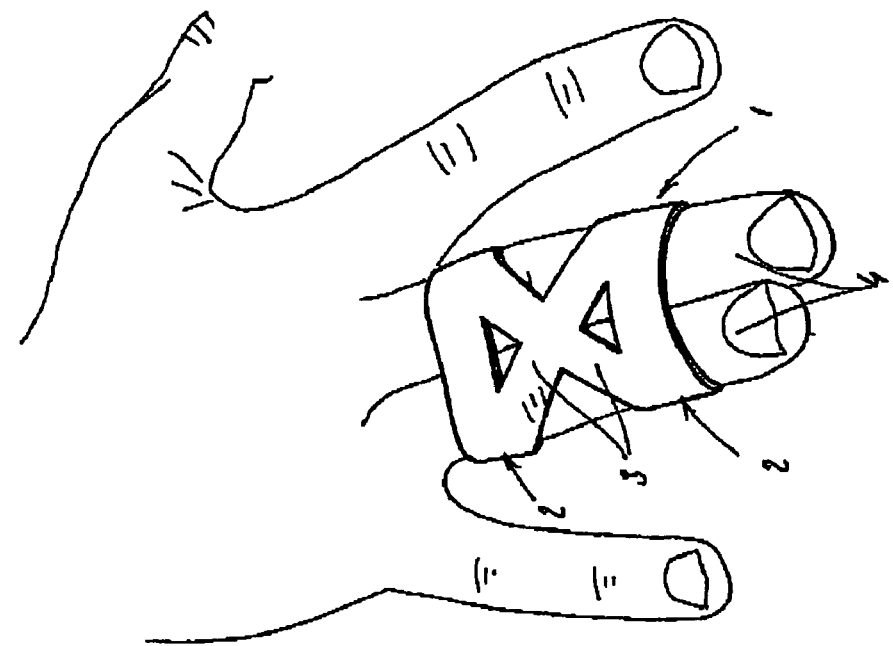
FIG. 3 is a plan view, in perspective, of a device with a double intersecting bar according to the invention, positioned on a patient's hand.

The device 1 for syndactyly of at least two fingers or toes according to the invention comprises at least two flexible rings 2 joined via at least one flexible connection bar 3 in such a way as to permit sliding of the syndactylized fingers or toes 4 relative to one another. In the description which follows, reference will be made to syndactyly of fingers, but this is not in any way a restrictive description of the invention, the latter being intended preferably for syndactyly among the first four fingers of the hand, and among the five toes.

According to an important characteristic of the invention, the device 1 permits sliding of the syndactylized fingers 4 relative to one another during the flexion/extension movement of said fingers. This independence of the syndactylized fingers 4 in terms of sliding makes it possible to maintain a reduced but essential mobility of the injured finger, at least in one plane. Thus, healing is possible by virtue of the mainly lateral supporting of the injured finger by the adjacent finger or fingers, and, at the same time, early rehabilitation is possible because the motricity of the injured finger is preserved, at least as regards the flexion/extension movements. Healing is thus possible without affecting motricity. Such sliding of the fingers relative to one another is effected when, in complete flexion of the hand, the extremities of the last four fingers are aligned, as is shown in FIG. 6, which is not the case when the hand is in extension, even partial extension.

This device 1 is preferably molded flat in one piece, preferably by injection of a thermoplastic elastomer with resilient properties. Such properties of resiliency permit high-quality syndactyly, that is to say effective joining of an injured finger to one or more adjacent fingers, while at the same time maintaining a pliability and stretchability allowing for easy fitting and removal. In addition, the elasticity of the rings of the device according to the invention allows the syndactylized fingers 4 to slide relative to one another, which, as has already been explained above, is an essential component of the device of the invention.

If appropriate, it is possible for the syndactyly device 1 of the invention to be made by dual injection, that is to say sequential injection of two different plastics in the same mold. Thus, the rings 2 can be molded from a first elastic material in order to permit positioning and withdrawal around the fingers and also a good hold when the ring is positioned around the fingers, and the bar 3 joining them can be molded from a flexible but nonelastic material, so as to keep the distance between the two rings 2 of the device 1 constant at all times.

In all cases, the material chosen to make the device of the invention is preferably a nonallergenic material.

Figure 2:
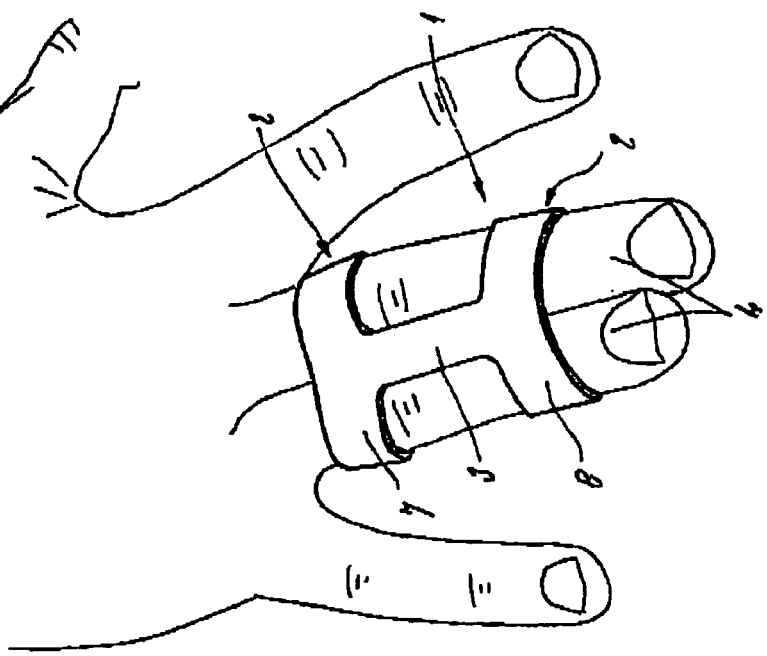
FIG. 2 is a plan view, in perspective, of the device from FIG. 1, positioned on two fingers of a patient's hand.

According to a first embodiment of the invention, as represented in FIGS. 1, 2 and 6, the syndactyly device 1 according to the invention comprises a single connection bar 3 arranged between at least two rings 2.

According to a second embodiment of the invention, as represented in FIG. 3, the syndactyly device 1 according to the invention comprises two intersecting connection bars 3 arranged between at least two rings 2.

Figure 5:
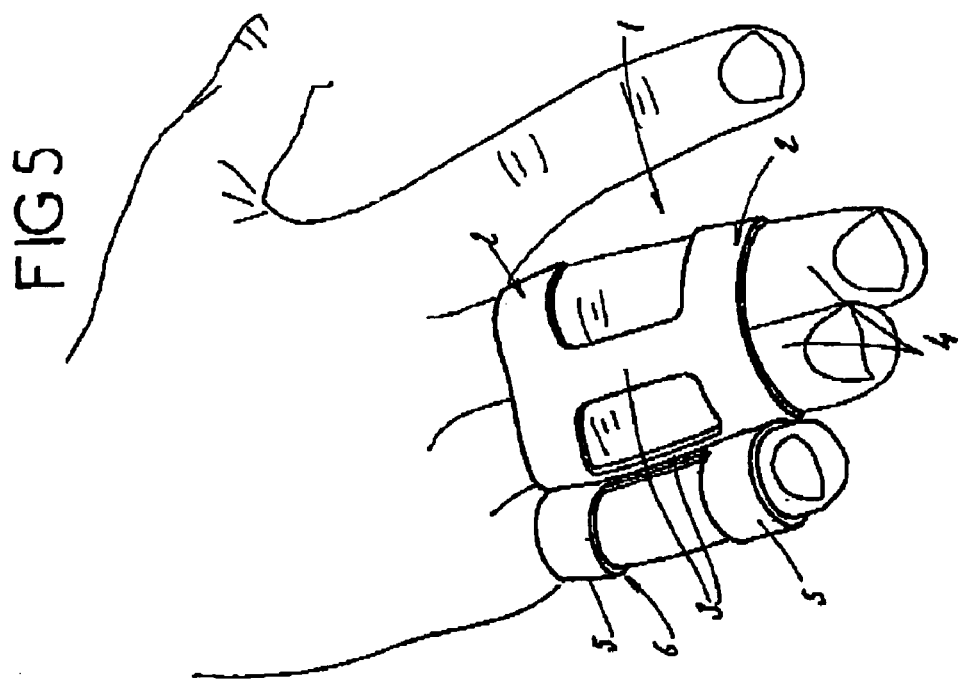
FIG. 5 is a plan view, in perspective, of two devices according to the invention paired together and positioned around a patient's fingers.
Figure 4:
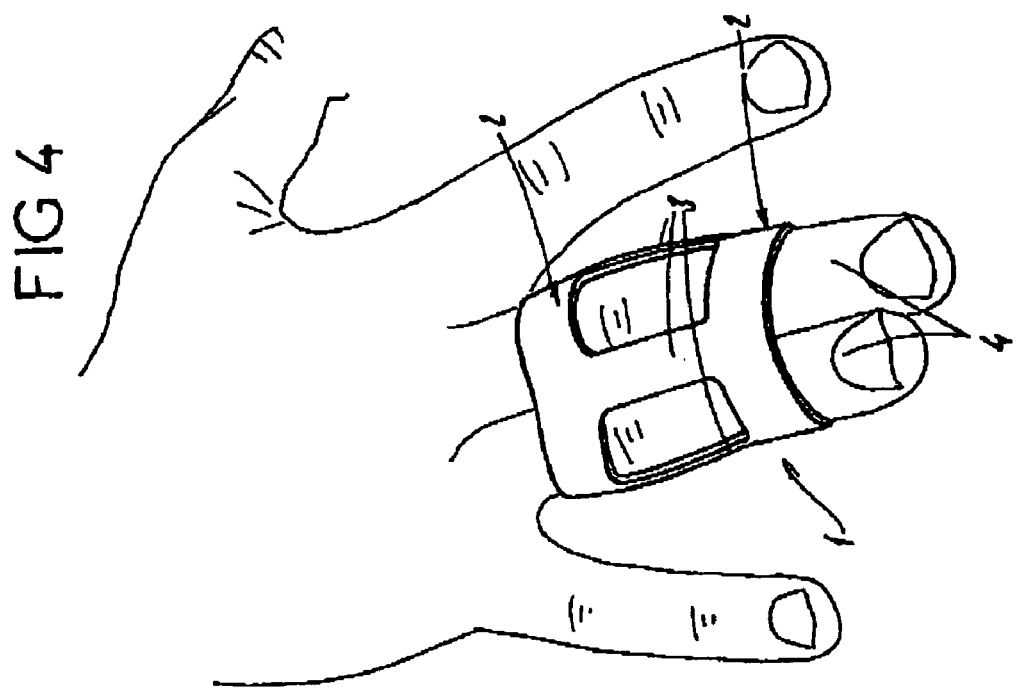
FIG. 4 is a plan view, in perspective, of a second device according to the invention with an upper bar and two lateral bars, positioned on a patient's hand.

According to a third embodiment of the invention, represented in FIGS. 4 and 5, the device 1 comprises at least two connection bars 3 parallel to one another and arranged between at least two rings 2.

In each of the different embodiments of the invention which have been described above, each bar 3 of the device 1 is a dorsal and/or lateral bar, that is to say the bar or bars is/are intended to be arranged on the dorsal aspect of the hand or foot, and/or if appropriate on the lateral aspect of the group of syndactylized fingers. The reason for this is that if a bar were to be placed on the palmar aspect of the hand or foot, this would be subject to very uncomfortable folding for the patient during the flexion movements.

In a particular embodiment of the device according to the invention, as represented in FIG. 4, the rings 2 of the device 1 can be integral with the rings 5 of a second syndactyly device 6, or, alternatively, they can be integral with rings 5 fitted round a healthy finger.

As will be seen from FIGS. 2 through 5, a syndactyly performed with the aid of the device according to the invention is achieved by successively engaging the rings 2 of the device 1 simultaneously about the fingers 4 to be syndactylized. The distance between the rings 2 is determined by the length of the connection bar 3. The diameter of the rings 2 is calculated to correspond approximately to the sum of the diameters of the fingers 4 to be syndactylized. In any event, the person skilled in the art will be able to adapt this diameter as a function of the size of the patient's fingers, and also the width of the rings 2, so that the connection between the two adjacent fingers is achieved without play (that is to say the ring is slightly tensioned once placed around the fingers), while at the same time permitting correct circulation of blood in the fingers and allowing sliding of the fingers relative to one another. Similarly, the thickness of the rings will be able to be adapted according to the desired elastic force, as a function of the therapeutic indication.

Similarly, the length of the connection bar 3 will have to be chosen to permit adaptation of the syndactyly device 1 according to the invention in the following way. The ring of greater diameter 7 is fitted first and arranged around the proximal phalanges of the fingers to be syndactylized 4, then the ring of smaller diameter 8 is fitted around the distal phalanges of the fingers to be syndactylized 4, so that the connection bar or bars 3 is/are arranged over the articulation between said proximal and distal phalanges. In this way, it is possible to freely choose to place the device around the first or second interphalangeal articulation of the injured finger.

Finally, it should be noted that the device according to the invention is intended to be used when at least some of the patient's fingers are covered with dressings, for example in the case of burns. In this case, however, it will be necessary to adapt the diameter of the rings of the device.

While it has been sought, in the above description, to draw attention to those characteristics of the invention which are judged to be of particular importance, it should be noted that the invention is not limited to the embodiment described above, and that instead it encompasses all variants thereof. Thus, in particular, the number and arrangement of the connection bars can be adapted as a function of the morphology of the patient, or as a function of the rehabilitation to be effected.

The invention claimed is:

1. A medical device for syndactyly of at least two fingers or toes, said device being in one piece and comprising at least two flexible rings joined via two intersecting connection bars arranged between the at least two flexible rings in such a way as to permit sliding of the syndactylized fingers or toes relative to one another.

2. The syndactyly device as claimed in claim 1, wherein each bar of the device is a dorsal and/or lateral bar.

3. The syndactyly device as claimed in claim 2, said device being made of a single elastomeric material with resilient properties.

4. The syndactyly device as claimed in claim 2, said device being made of two materials, one flexible for the rings, and the other more rigid for the connection bars.

5. The syndactyly device as claimed in claim 1, said device being made of a single elastomeric material with resilient properties.

6. The syndactyly device as claimed in claim 1, said device being made of two materials, one flexible for the rings, and the other more rigid for the connection bars.

7. A medical device for syndactyly of at least two fingers or toes, said device being in one piece and comprising at least two flexible rings joined via at least two connection bars parallel to one another and arranged between the at least two flexible rings in such a way as to permit sliding of the syndactylized fingers or toes relative to one another.

8. The syndactyly device as claimed in claim 7, wherein each bar of the device is a dorsal and/or lateral bar.

9. The syndactyly device as claimed in claim 8, wherein the rings of the device are integral with a second syndactyly device.

10. The syndactyly device as claimed in claim 9, said device being made of a single elastomeric material with resilient properties.

11. The syndactyly device as claimed in claim 9, said device being made of two materials, one flexible for the rings, and the other more rigid for the connection bars.

12. The syndactyly device as claimed in claim 8, said device being made of a single elastomeric material with resilient properties.

13. The syndactyly device as claimed in claim 8, said device being made of two materials, one flexible for the rings, and the other more rigid for the connection bars.

14. The syndactyly device as claimed in claim 7, wherein the rings of the device are integral with a second syndactyly device.

15. The syndactyly device as claimed in claim 1, said device being made of a single elastomeric material with resilient properties.

16. The syndactyly device as claimed in claim 7, said device being made of two materials, one flexible for the rings, and the other more rigid for the connection bars.

* * * * *